United States Patent [19]

Bruno

[11] Patent Number: 5,070,024
[45] Date of Patent: Dec. 3, 1991

[54] HYDROCARBON DETECTOR UTILIZING CATALYTIC CRACKING

[75] Inventor: Thomas J. Bruno, Broomfield, Colo.

[73] Assignee: Gas Research Institute, Chicago, Ill.

[21] Appl. No.: 218,088

[22] Filed: Jul. 12, 1988

[51] Int. Cl.$^5$ ............................................. C01N 27/16
[52] U.S. Cl. ................................... 436/139; 436/140; 436/141; 436/142; 436/143; 436/159; 422/93; 422/94
[58] Field of Search ........ 436/159, 147, 139, 140–143; 73/23.32, 23.4; 422/90, 93, 94

[56] References Cited

U.S. PATENT DOCUMENTS

| | | | |
|---|---|---|---|
| 3,488,155 | 1/1970 | Ayers | 23/232 |
| 3,725,005 | 4/1973 | Innes | 23/232 E |
| 3,939,058 | 2/1976 | Plank et al. | 208/120 |
| 4,170,455 | 10/1979 | Henrie | 23/232 R |

OTHER PUBLICATIONS

CA 107(18):167995t, "Catalytic Cracking as the Basis for a Potential Detector for Gas Chromatography".

Primary Examiner—David L. Lacey
Assistant Examiner—David Redding
Attorney, Agent, or Firm—Donald W. Margolis; James R. Young

[57] ABSTRACT

A hydrocarbon gas detection system utilizes a heat chamber or oven to maintain the system at a temperature that will support cracking of hydrocarbon gases. A gas chamber which is located inside the oven is used to contain the flow of gases under analysis and to pass these gases over a first temperature sensing device. A catalyzing material is associated with the first temperature sensing device, either by placing it very near the temperature sensing device or by coating the temperature sensing device with the catalyzing material. A second temperature sensing device is located inside the heat chamber or oven, either outside the gas chamber, or inside the gas chamber, but separated from the first temperature sensing device. The output of the first and second temperature sensing devices extend outside of the furnace to measurement and/or display instrumentation. With this system, the gas sample under analysis is passed through the gas chamber and brought into contact with the first temperature sensing device. The catalyzing material associated with the first temperature sensing device causes cracking of any hydrocarbon gases. This cracking reaction changes the temperature of the first temperature sensing device which, together with the second temperature sensing device, causes an output voltage proportional to the change in temperature. The amount of voltage output by the system is proportional to the amount and type of hydrocarbon present in the gas sample under analysis.

17 Claims, 2 Drawing Sheets

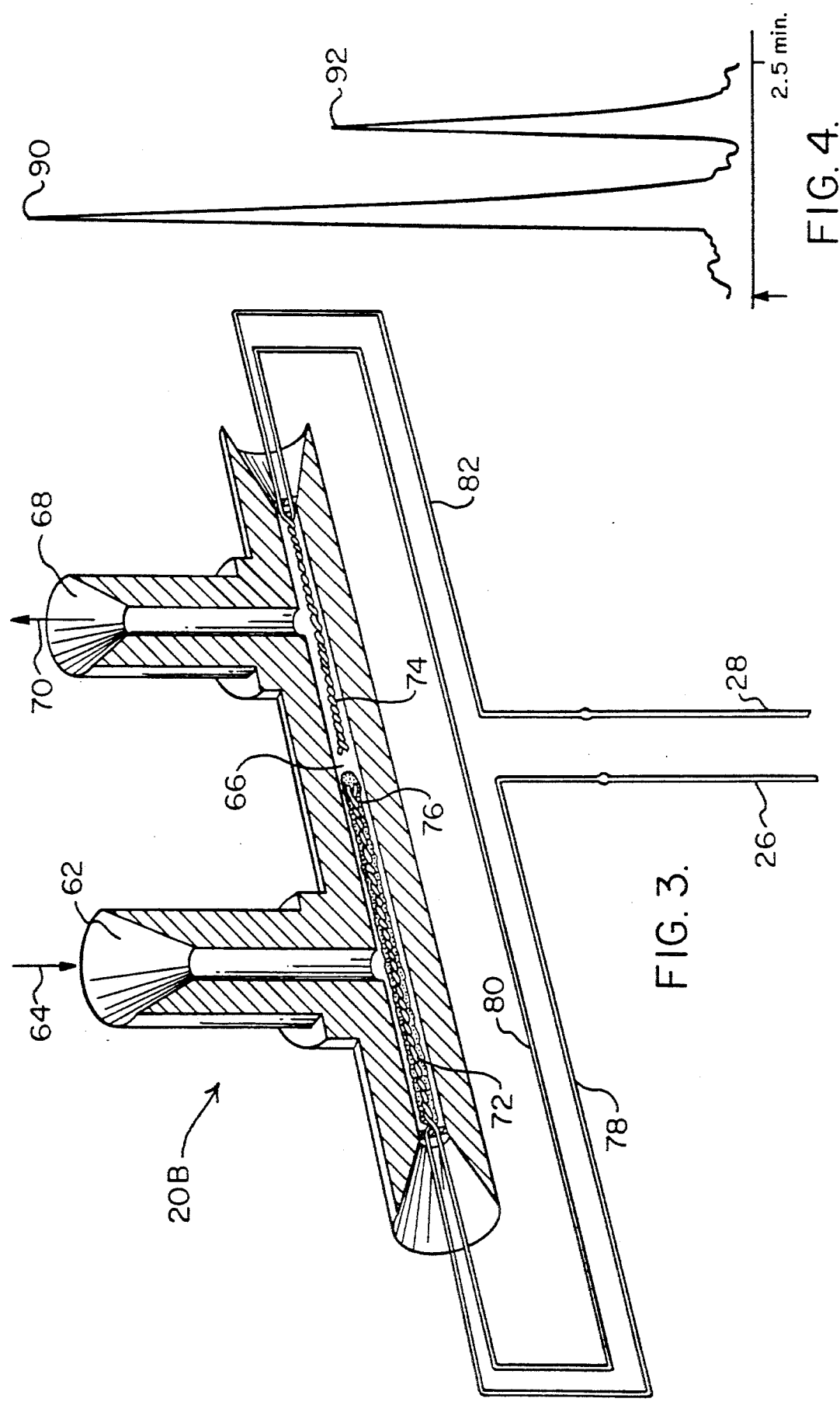

HYDROCARBON DETECTOR UTILIZING CATALYTIC CRACKING

The invention described herein may be manufactured and used by or for the Government of the United States for all governmental purposes without the payment of any royalty.

BACKGROUND OF THE INVENTION a) Field of the Invention

This invention relates to sensors for detecting components of a gas or vapor. More particularly, it relates to detection of hydrocarbon components from a gas chromatographic column. Even more particularly, it relates to an improved thermoelectric device design for detecting an analyte undergoing a catalyzed endothermic reaction.

b) Discussion of the Prior Art

The use of heat sensing devices, such as thermocouples, to detect temperature and temperature changes is well known in the art. Associating a catalyst with the hot junction of a thermocouple to improve its output is also known in the art, for example see Tracht U.S. Pat. No. 3,070,645, in which a catalyst was added to the hot junction of each of the thermocouples in a thermopile in a device to directly convert thermal energy into electrical energy.

Thermocouple systems have also been considered for use as automobile exhaust gas analyzers, operating on the principle that heat generated by completely oxidizing residual combustibles in automobile exhaust gases is proportional, within certain limits, to the concentration of residual combustibles in the automobile exhaust gases. In this regard, and of perhaps greatest interest to the present invention is, U.S. Pat. No. 3,906,721 to Micheli, et al teaches a temperature detector in which the hot and cold junctions of a thermocouple are embedded in a U-shaped ceramic body and mounted in the exhaust system of an automobile. An automobile exhaust system places particular requirements on this type of sensor, because the exhaust gases cool rapidly as they move away from the engine. As a result of this requirement, the Micheli patent describes a device wherein both junctions of the thermocouple are formed in a single U-shaped ceramic body, and this body is placed in the exhaust system perpendicular to the flow of exhaust. Therefore, the exhaust gases which pass both sides of the thermocouple are at the same distance from the engine at the same time, so both junctions of the thermocouple remain at the same temperature, unless one junction reacts with the gases. The difficulty of this system consists of the expense of manufacturing both thermocouple junctions simultaneously, and the requirement that both thermocouple junctions contact the exhaust gases at the exact same point in the exhaust system. The ceramic U-shaped element also makes this detector physically large. Furthermore, since both junctions of the thermocouple are within the stream of the exhaust gas they are both subject to corrosion and abrasion by the gas.

The device of Micheli U.S. Pat. No. 3,906,721 cannot be easily applied as detector for use with a gas chromatograph. In chromatographic detection, analytes are often present at extremely high dilution, and therefore the size of any detection cell used must be carefully minimized, while maintaining good sensitivity. Additionally, the configuration and size of the device of Micheli U.S. Pat. No. 3,906,721 is much too large to be applied to chromatographic detection, and could not be reduced to a useful size without producing a much more complex device, By contrast, and as detailed below, the size of the detection cell used in the device of the present invention is extremely small and inherently simple.

The catalyst used in the device of Micheli U.S. Pat. No. 3,906,721 is completely different from the catalyst used in the device of the present invention. In the device of the Micheli patent, a platinum based catalyst is used since such a catalyst optimizes the oxidation process which the device of the Micheli patent monitors.

Furthermore, the mechanism of operation of the device of Micheli U.S. Pat. No. 3,906,721 is completely different from the mechanism of operation of the device of the present invention. The device of the Micheli patent depends upon catalytic oxidation in which two chemical species, a hydrocarbon molecule and an oxidant molecule, combine in an exothermic reaction to form a new chemical species. In the device of the present invention a single chemical species, a hydrocarbon molecule, by itself, undergoes endothermic catalytic cracking to form two or more hydrocarbon species. The device of the Micheli patent requires that more than one chemical species be present in the process stream, for example a hydrocarbon and an oxidant. Therefore, the device of the Micheli patent would be ineffective in analyzing the gas stream which leaves the typical chromatographic column, since such a gas stream consists of a single, separated gas component eluant in an inert gas carrier. Oxidants are substantially never present in such a chromatographic eluent stream with hydrocarbons, and if they were, the presence of oxidant in a predominantly hydrocarbon stream would at best impair chromatographic operation, and, at worst, could destroy apparatus components and create a potentially explosive hazard. In hind site, in order to render the device of the Micheli patent suitable for use as a detector for chromatography, would require that a controlled concentration of oxidant be added to the process stream, which is neither suggested by Micheli, nor a routine change, in such a system because of the hazards, and which further is not believed to be possible using state-of-the-art instrumentation.

For completeness of this discussion, it should be noted that, while there are some chromatographic detectors which require the application of an oxidant for operation, the oxidant is applied outside of the eluent or process stream, and therefore does not dilute the eluent or process stream.

It is thus seen that it would be desirable to have an improved thermoelectric detection system which resolves these problems.

SUMMARY OF THE INVENTION

In view of the foregoing, it is an object of the present invention to provide an improved thermoelectric gas sensor for detecting the presence of crackable hydrocarbon gases.

It is another object of the present invention to provide such a device which is very small in size.

Another object of the present invention is to provide a thermoelectric gas sensor system for detecting the presence of crackable hydrocarbon gases, which system is simple in construction and design, and which lends itself to chromatographic analysis.

It is still another object of the present invention to provide such a sensor wherein only one of the junctions is exposed to the gases under analysis, and therefore exposed to corrosion and abrasion, while the other junction of the thermocouple, although maintained at the temperature of the gases, is sealed from exposure to the gases.

It is yet another object of the present invention to provide a simple, inexpensive system for chromatographic analysis.

Another object of the present invention is to provide a gas chromatographic detector which is far more simple in design and operation than commonly available commercial detectors.

The foregoing objects of the present invention are obtained by providing a gas detection system wherein a heat chamber, or oven, is used to maintain the entire system at a temperature that will support the cracking activity. A gas chamber, located inside the oven is used to contain the flow of the gases under analysis, and to pass these gases over a first temperature sensing device. A second temperature sensing device is located inside of the over, outside of the gas chamber, but mounted on the gas chamber or in close proximity thereto. A material which catalyzer hydrocarbon cracking is associated with the first temperature sensing device, either by placing it very near to the first temperature sensing device or by physically connecting it with the first temperature sensing device. In preferred embodiments the first temperature sensing device will be a first temperature sensing thermocouple, hereinafter sometimes referred to as a "first junction", and the second temperature sensing device will be second, or a reference, thermocouple, hereinafter sometimes referred to as a "second junction." As used herein the combination of a first temperature sensing device and a second temperature sensing device, or the combination of a first junction and a second junction is referred to as a "heat sensing device." The electrical output of any such heat sensing device extends outside of the furnace to measurement and/or display instrumentation. In this system, then, the gas under analysis, usually contained within a carrier gas, is passed through the gas chamber and brought into contact with the first junction of the thermocouple. The catalyzing material associated with the first junction causes endothermic cracking of any hydrocarbon gases contained in the gas under analysis. This endothermic reaction removes heat from the first junction of the thermocouple, causing the thermocouple to output a voltage proportional to the drop in temperature. The amount of voltage output by the thermocouple is proportional to the amount and type of hydrocarbon present in the gas sample.

Additionally, all known detectors commonly used with gas chromatographs are substantially more complex than the present invention. The present invention requires no ancillary electronics for its operation. For example, in this respect, it differs from standard thermal conductivity detectors in that it requires no electronic balance bridge. It differs from the standard flame ionization detector in that it requires no electrometer. In addition to the two common detectors mentioned above, the present invention is also far simpler than the electron capture, flame photometric, mass selective, gas density balance, and photoionization chromatographic detectors which are currently used in the art.

These and other objects of the present invention will become apparent to those skilled in the art from the following detailed description, showing the contemplated novel construction, combination, and elements as herein described, and more particularly defined by the appended claims, it being understood that changes in the precise embodiments of the herein disclosed invention are meant to be included as coming within the scope of the claims, except insofar as they may be precluded by the prior art.

BRIEF DESCRIPTION OF THE DRAWINGS

The accompanying drawings illustrate complete preferred embodiments of the present invention according to the best modes presently devised for the practical application of the principles thereof, and in which:

FIG. 3 shows a detail of a second embodiment of the catalytic cracking detector system wherein a pair of temperature sensing devices are in contact with the to-be-treated gas; and FIG. 4 is a sample chromatogram showing the information output of the catalytic cracking detector of the present invention in response to a hydrocarbon sample.

DESCRIPTION OF THE PREFERRED EMBODIMENT

The following description is of the best presently contemplated modes of carrying out the present invention. This description is not to be taken in a limiting sense but is made merely for the purpose of describing the general principles of the invention. The scope of the invention should be determined with reference to the appended claims.

The functional principle of the detector of the present invention relies on the measurement of the temperature change of a catalyst as catalytic cracking occurs at the catalyst. This measurement is performed by passing the gas under analysis, through a gas chamber containing at least a first junction of a heat sensing device. This first junction may be coated with a catalyst, or such a catalyst is otherwise associated with the first junction in a manner such that a change in temperature of the catalyst will be sensed by the first junction. A second junction of the heat sensing device is maintained at the same temperature conditions as the first junction and as the gas under analysis. The second junction may be either in contact with or out of contact with the gas undergoing analysis, is contained inside or outside the chamber. If the gas under analysis contains crackable hydrocarbons, and the catalyst is maintained at a temperature which will support cracking, then catalytic cracking of the hydrocarbons occurs on the surface of the catalyst. While the mechanism is not understood with certainty, heat is normally found to be extracted from the catalyst when cracking occurs. Since the catalyst is either coated on or in thermally detectable proximity to the first heat sensing device junction, heat is also drawn from the first junction. Since heat has been removed from the first junction and the second junction which does not have a catalyst associated with it, is maintained at the same temperature, a temperature difference will exist between the first and second heat sensing device junctions when cracking occurs. This temperature differential will cause the heat sensing device to output a differential electrical voltage, not equal to zero. The output voltage of the heat sensing device can then be measured and/or plotted using state of the art instruments. Analysis of those measurements or plots will show the amount and type of crackable hydrocarbon, if any, present in the gas under analysis.

Figure 1:
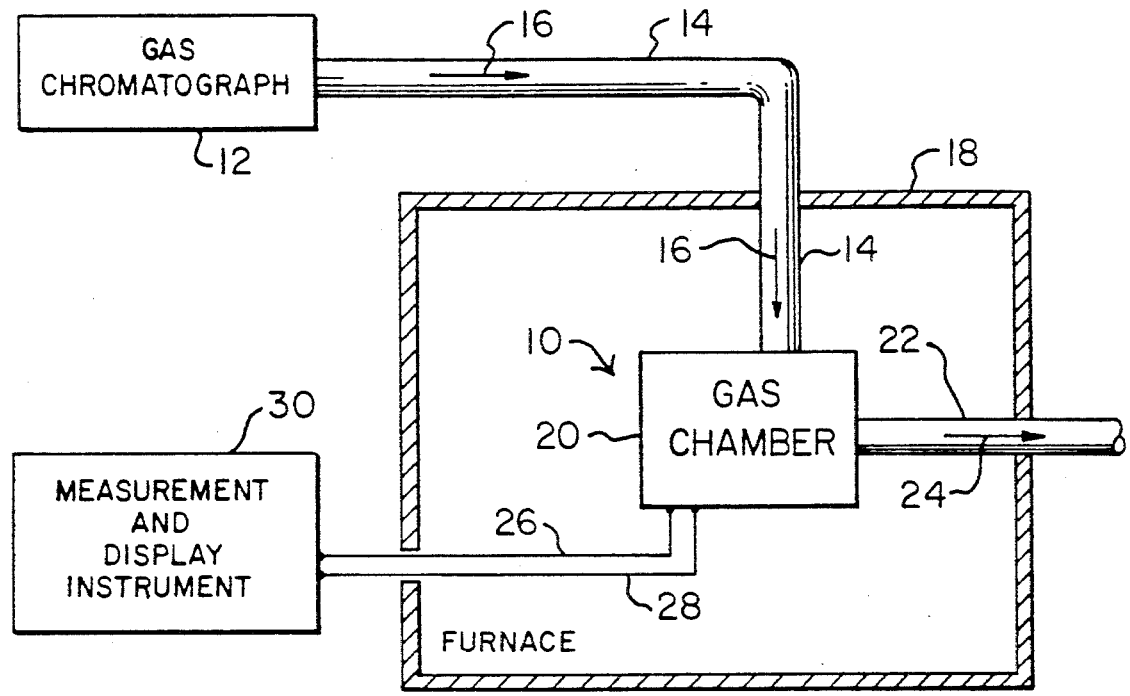
FIG. 1 provides a diagrammatic representation of the catalytic cracking detection system according to the present invention, in conjunction with a gas chromatograph and a measurement and display system.
Figure 2:
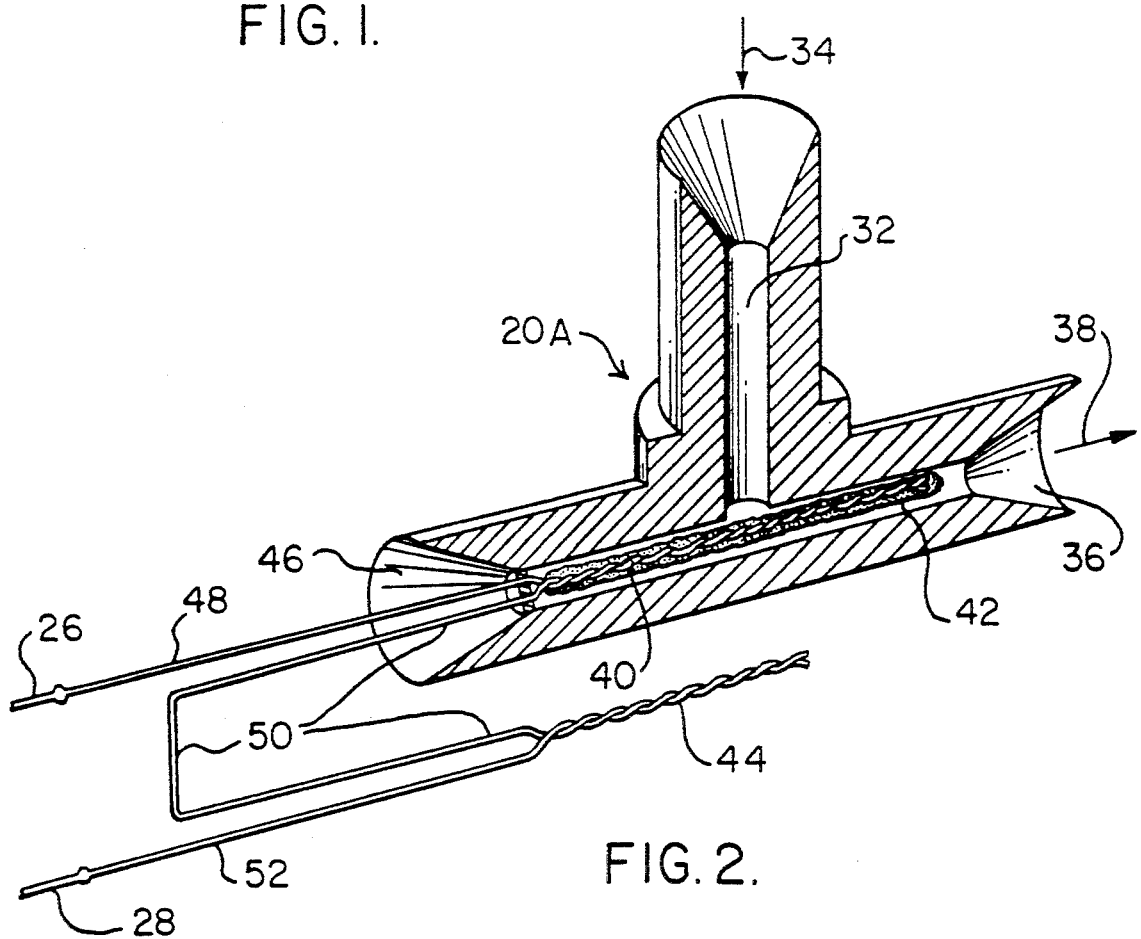
FIG. 2 shows the details of one embodiment of the catalytic cracking detector system of the invention wherein a first temperature sensing device is located inside a gas chamber, and a second temperature sensing device is located in contact with a to-be-treated gas and a second temperature sensing device is out of contact with the gas.

Now referring to the drawings, FIG. 1 provides a diagrammatic representation of the catalytic cracker detection system, generally 10. In this embodiment, to-be-tested gas from gas chromatograph 12 passes through tube 14 in the direction of arrow 16, through the wall of furnace 18. A length of the portion of tube 16 which is inside of furnace 18 is long enough to preheat the gas under analysis before it enters gas chamber 20. The gas passes through gas chamber 20 and then out through an exit tube 22 in the direction of arrow 24. As the to-be-treated gas passes through gas chamber 20, it contacts one or more junction of a heat sensing device, which in the preferred embodiments shown in FIGS. 2 and 3 is a first and second thermocouple junction. With respect to the several embodiments, greater details are set forth below. Since the heat sensing device, not shown in FIG. 1, is also within furnace 18 it is also heated. The temperature of furnace 18 and of the heat sensing device and the gas is maintained at a temperature which will support catalyzed cracking of a crackable hydrocarbon, say about 500 C. (932 F.) to about 600 C. (1112 F.). Thus, if crackable hydrocarbons are present an endothermic catalyzed cracking reaction will occur at the catalyst associated with the first junction of heat sensing device 20. This will cause heat sensing device 20 to output a voltage signal on wires 26 and 28. Signal wires 26 and 28 pass out of furnace 18 and into measurement and display instrument 30 whereby the voltage may be measured, recorded or displayed to indicate the presence or absence of a specific hydrocarbon in the gas from chromatograph 12 which is undergoing analysis.

FIG. 2 shows a more detailed drawing of one form of gas chamber 20, wherein gas passes into chamber 20 through inlet 32 in the direction of arrow 34, and out through outlet port 36 in the direction of arrow 38. A first junction 40 of a thermocouple temperature sensing device is present in chamber 20. Junction 40 is associated with a catalyst, in this case in the form of coating 42. As the gas passes through chamber 20, it comes into contact with the surface of coating catalyst 42. A second junction 44 of the thermocouple temperature sensing device is bonded to gas chamber 30 using, for example, a high temperature adhesive 46, such as a zirconia based adhesive. Zirconia based adhesive is also used to attach first junction 40 to the inside of gas chamber 20, and to seal its entryway. First thermocouple junction 40 is made of a heat and electrically conductive nickel-chromium alloy wire 48, such as Chromel, and nickel-manganese-aluminum-silicon, iron alloy wire 50, such as Alumel. Second wire 50 of first junction 40 also form a wire portion of second thermocouple junction 44. First wire 52 of second thermocouple junction 44 is also made typically of Chromel.

When crackable hydrocarbons are present in the gas flowing through chamber 20 cracking will occur at the surface of catalyst 42. Cracking on the surface of catalyst 42 will cause a temperature change in the catalyst. This temperature change in the catalyst will cause a corresponding temperature change in first thermocouple junction 40. Since second thermocouple junction 44 is not in contact with the gas, cracking will not occur in its vicinity and its temperature will not change. Therefore, when catalytic cracking occurs within chamber 20 a temperature difference will exist between junctions 40 and 44 of the thermocouple. Any temperature difference between junctions 40 and 44 of the thermocouple will cause the thermocouple to generate a voltage, the voltage being proportional to the temperature differential. This voltage will be transmitted from furnace 18 by signal wire 26 and 28 to measurement device 30, where it can be measured or plotted to indicate the presence of crackable hydrocarbons by a catalytic reaction.

FIG. 3 shows an alternative embodiment of the present invention utilizing a different form of gas chamber 60. In this embodiment the gas undergoing analysis enters chamber 60 through an inlet port 62 in the direction of arrow 64 into an inner chamber 66. The gas passes through inner chamber 66 and out through outlet port 68 in the direction of arrow 70. As the gas passes through inner chamber 66, it passes over both first temperature sensing thermocouple junction 72, and second temperature sensing thermocouple 74. First junction 72 is associated with a catalyst, in this case once again coating 76. Second junction 74 has no catalytic material associated with it. When there are certain crackable hydrocarbons present in the gas under analysis, an endothermic catalytic cracking reaction will occur on the surface of catalyst 76, thus lowering the temperature of catalyst 76 which in turn will lower the temperature of first junction 72. As gas passes through inner chamber 66 it also comes in contact with second thermocouple junction 74. However, no reaction occurs at junction 74 since it has no catalyst associated with it. Since the gas passes both the first junction 72 and the second junction 74, both junctions will be maintained at the same temperature, unless catalytic cracking occurs in association with first junction 72.

As in the embodiment of FIG. 2, first junction 72 is made up of first wire 78, which is typically made of Alumel, and a second wire SO, which is typically made of Chromel. Second wire 80 of first junction 72 is also one of the wires of second junction 74.

When a difference in temperature exists between first junction 72 and second junction 74, an output voltage occurs and is output through signal wires 26 and 28. This output voltage is sent to a measuring instrument where it is displayed, recorded or plotted to indicate the presence of crackable hydrocarbons in the gas undergoing analysis.

One hydrocarbon cracking catalyst which can be used in the catalytic cracking detector of the present invention is a mixture of 70 percent silicon dioxide, 20 percent aluminum oxide, and 10 percent sodium alumino-silicate (13-X type molecular sieve). A thin layer of the mixture in a water base can be coated on the twisted strands of the first heat sensing device junctions 40 and 72 of the embodiments shown in FIGS. 2 and 3, respectively.

A sample chromatogram showing the detector response of the present invention to 5 microliters of a mixture of n-hexane and n-octane (60/40 approximate mole percent) is shown in FIG. 4. The separation was performed, using the detector of FIG. 3, on a three meter packed column of Porapak-QS porous polymer, at a column temperature of 200 C., using helium as the carrier gas, at a flow rate of 30 milliliters per minute. The measuring device was set for a full-scale sensitivity of 8 microvolts. Thus, the peaks obtained correspond to a catalyst temperature drop of between 0.12 C. and 0.16 C. Referring to FIG. 4, the peak 90 shows the chromatogram response to n-hexane, and the peak 92 shows the response to n-octane. The response of the detector is selective for crackable hydrocarbons. Thus, samples of n-butane and propane were unresponsive, as was a mixture of fluorinated hydrocarbons. The detector responds also to alkyl substituted aromatic hydrocarbons, with the response increasing with the size of alykl substituent.

After several weeks of operation, a deposit of coke was found to have formed upon the surface of the coated junction. This was expected, since coke formation always occurs in commercial riser crackers. The coke layer did not cause a noticeable decrease in the activity of the detector, probably because of the relatively small quantity of hydrocarbon undergoing reaction in the detector relative to that in commercial situations. The coke layer is easily burned off in the presence of air which may be injected using a syringe, of the type used to inject any analytical sample.

It is thus seen that the present invention provides an improved thermoelectric gas sensor for detecting the presence of crackable hydrocarbon gases. The thermoelectric gas sensor of the present invention can be very small in size, is simple in construction and design, and is inexpensive to construct and maintain. It especially lends itself to use for chromatographic analysis. It is clearly far more simple in design and operation than commonly available commercial detectors.

While the invention has been particularly shown, described and illustrated in detail with reference to preferred embodiments and modifications thereof, it should be understood by those skilled in the art that the foregoing and other modifications are exemplary only, and that equivalent changes in form and detail may be made therein without departing from the true spirit and scope of the invention as claimed, except as precluded by the prior art.

What is claimed is:

1. A system for use in detecting the presence of crackable hydrocarbon gases by detecting the existence of a cracking reaction, said system comprising:
    a heat chamber means for maintaining a temperature which will support hydrocarbon cracking activity;
    a gas chamber means located in said heat chamber means for receiving to-be-analyzed gases;
    a heat sensing device located within said heat chamber means, said heat sensing device including in combination;
        first means for sensing temperature, said first temperature sensing means being located within said gas chamber means;
        second means for sensing temperature, said second temperature sensing means being located within said heat chamber means; and
        electrical signal output means for sensing electrical signals, said electrical signal output means being connected to both said first and second temperature sensing means;
    hydrocarbon cracking catalyzing material associated in thermally responsive relation with said first means for sensing temperature, said hydrocarbon cracking catalyzing material serving to catalyze the cracking of hydrocarbon gases when such gases are present in said gas chamber means and in contact with said hydrocarbon cracking catalyzing material and said heat chamber means is heated to a temperature which will support such cracking;
    measuring means connected to said electrical signal output means for sensing electrical signals produced by said heat sensing device;
    whereby when cracking of crackable hydrocarbon gases occurs the temperature of said catalyzing material and thence of said associated first temperature sensing means is changed, causing a temperature difference between said first and said second temperature sensing means, which in turn causes an electrical signal through said electrical signal output means, which electrical signal is measured by said measuring means, thus indicating the occurrence of said cracking, and the presence of crackable hydrocarbon gases.

2. The system of claim 1 wherein said second temperature sensing means is also located within said gas chamber means.

3. The system of claim 1 wherein said second temperature sensing means is located outside of said gas chamber means, yet within said heat chamber means.

4. The system of claim 1 wherein said first and second temperature sensing means are junctions of a thermocouple.

5. The system of claim 1 wherein said material for catalyzing the cracking of said hydrocarbon gases is coated onto at least a portion of said first temperature sensing means.

6. The system of claim 1 wherein said material for catalyzing the cracking of said hydrocarbon gases consists essentially of a mixture including zeolites.

7. The system of claim 6 wherein said mixture includes silicon dioxide, aluminum oxide, and sodium alumino-silicate zeolite.

8. The system of claim 7 wherein said mixture consists of about 70% silicon dioxide, about 20% aluminum oxide, and about 10% sodium alumino-silicate, all by weight.

9. The system of claim 1 wherein said gas chamber means has gas inlet and gas outlet ports.

10. The system of claim 9 wherein means for conveying gas are connected to said gas inlet port for bringing to-be-analyzed gases into said gas chamber means.

11. The system of claim 1 wherein said electrical signal is a non-zero voltage.

12. A system for use in detecting the presence of crackable hydrocarbon gases by detecting the existence of a cracking reaction, said system comprising:
    a heat chamber means for maintaining a temperature which will support cracking activity;
    a gas chamber means located within said heat chamber means, said gas chamber means having gas inlet and gas outlet ports;
    a thermocouple comprising,
        a first junction located within said gas chamber means,
        a second junction comprised of Chromel and Alumel wires within said heat chamber means, and
        electrical signal output means for sensing electrical signals, said electrical signal output means being connected to both said first and second thermocouple junctions;
    catalyzing material bonded to said first thermocouple junction for catalyzing the cracking of said hydrocarbon gases, said catalyzing material consisting essentially of a mixture of about 70% silicon dioxide, about 20% aluminum oxide, and about 10% sodium aluminosilicate, all by weight;

means for conveying gas connected to said inlet port to bring gas into said gas chamber means; and means for measuring a voltage produced by said thermocouple, and being connected to said thermocouple electrical signal output means;

whereby cracking in said gas chamber means changes the temperature of said first thermocouple junction causing a non-zero voltage on said thermocouple electrical output, thus indicating the occurrence of cracking, and the presence of crackable hydrocarbon gases.

13. A system for use in detecting the presence of crackable gases by detecting the existence of a cracking reaction, said system comprising:

a heat chamber means for maintaining a temperature which will support cracking activity;

a gas chamber means for receiving to-be-analyzed gases, said gas chamber means located within said heat chamber means;

first means for sensing temperature, said first temperature sensing means being located within said gas chamber means;

second means for sensing temperature, said second temperature sensing means being located in juxtaposition with said first temperature sensing means and within said heat chamber means;

electrical signal output means connected to said first and second temperature sensing means; and cracking catalyzing material associated in thermally responsive relation with said first means for sensing temperature;

whereby when cracking occurs the temperature of said first temperature sensing means is changed causing a temperature difference between said first and said second temperature sensing means, which in turn causes an electrical signal output indicating the occurrence of said cracking, and the presence of crackable hydrocarbon gases.

14. The system of claim 13 wherein said second temperature sensing means is also located with said gas chamber means.

15. The system of claim 13 wherein said second temperature sensing means is located outside of said gas chamber means.

16. A process of determining whether a crackable gas is present by determining whether cracking is taking place within a gas composition, comprising the steps of:

placing said gas composition within a gas chamber means, which gas chamber means is within a heat chamber means for maintaining said gas chamber means at a temperature which will support hydrocarbon cracking activity;

placing a first means for sensing temperature inside said gas chamber means;

maintaining a second means for sensing temperature within said heat chamber means at a temperature substantially equal to the temperature inside said gas chamber means;

positioning a hydrocarbon cracking catalyzing material in thermally responsive relation with said first temperature sensing means; and measuring an electrical output from said first and second temperature sensing means;

whereby a predetermined electrical output from said first and second temperature sensing means indicates whether cracking is taking place, and therefore the presence of crackable hydrocarbon gases in the gas composition.

17. The process of claim 16 wherein said catalyzing material is coated onto at least a portion of said first temperature sensing means.

* * * * *